United States Patent
Eek et al.

(10) Patent No.: US 6,593,339 B1
(45) Date of Patent: Jul. 15, 2003

(54) USE OF COMPOUNDS AS ANTIBACTERIAL AGENTS

(75) Inventors: Arne Eek, Trosa (SE); Johan Raud, Bromma (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/673,007

(22) PCT Filed: May 25, 2000

(86) PCT No.: PCT/SE00/01071

§ 371 (c)(1),
(2), (4) Date: Sep. 29, 2000

(87) PCT Pub. No.: WO00/72838

PCT Pub. Date: Dec. 7, 2000

(30) Foreign Application Priority Data

Jun. 1, 1999 (SE) ............................................. 9902027
Dec. 21, 1999 (SE) ............................................. 9904704

(51) Int. Cl.$^7$ ...................... A61K 31/4439; A61P 29/00; A61P 31/04; A01N 29/00; A01N 29/32
(52) U.S. Cl. ...................... 514/303; 514/165; 514/166; 514/925; 514/926; 514/927
(58) Field of Search ................................. 514/165, 166, 514/925, 926, 927, 303

(56) References Cited

U.S. PATENT DOCUMENTS 4,758,579 A  7/1988  Kohl et al. .................. 514/338

FOREIGN PATENT DOCUMENTS

| EP | 0 005 129 | 10/1979 |
|----|-----------|---------|
| EP | 0 166 287 | 1/1986 |
| EP | 0 174 726 | 3/1986 |
| GB | 2 163 747 | 3/1986 |
| WO | WO 90/06925 | 6/1990 |
| WO | WO 93/00327 | 1/1993 |
| WO | WO 94/04484 | 3/1994 |
| WO | WO 94/12463 | 6/1994 |
| WO | WO 94/27988 | 12/1994 |
| WO | WO 95/01977 | 1/1995 |
| WO | WO 95/09612 | 4/1995 |
| WO | WO 95/09831 | 4/1995 |
| WO | WO 95/30641 | 11/1995 |
| WO | WO 97/31654 | 9/1997 |
| WO | WO 98/03219 | 1/1998 |
| WO | WO 98/22117 | 5/1998 |
| WO | WO 99/67210 | 12/1999 |

OTHER PUBLICATIONS

Soldato et al., "NO–releasing NSAIDs, a novel class of safe and effective anti–inflammatory agents", Inflammopharmacology 4, 1996, p. 181–188.
Warren JR, Lancet 1983, 1 p. 1273.
STN International, CAPLUS Accession No. 1999:500417.
Davies et al., "NO–naproxen vs. naproxen: ulcerogenic, analgesic and anti–inflammatory effects", Aliment Pharmacol. Ther. vol. 11, 1997, p. 69–79.
Schmassmann, "Mechanisms of ulcer healing and effects of nonsteroidal anti–inflammatory drugs", Am. J. Med., vol. 104, No. 3A, 1998, p. 43S–51S.
Fiorucci et al., "Nitric oxide–releasing NSAIDs inhibit interleukin–1. Beta.converting enzyme–like..", Alim. Pharma. Ther. vol. 13, 1999, p. 421–435.
English language abstract of SR above.
Elliott, et al., "A Nitric Oxide–Releasing Nonsteroidal Anti- -Inflammatory Drug Accelerates Gastric Ulcer Healing in Rats," *Gastroenterology* 109:524–530 (1995).

*Primary Examiner*—Frederick Krass
*Assistant Examiner*—Clinton Ostrup
(74) *Attorney, Agent, or Firm*—Michael A. Sanzo; Fitch, Even, Tabin & Flannery

(57) ABSTRACT

The present invention discloses a new use of NO-releasing NSAIDs, especially NO-releasing NSAIDs of the formula I, or a pharmaceutically acceptable salt or enantiomer thereof, for the manufacture of a medicament for the treatment of bacterial infections, especially caused or mediated by *Helicobacter pylon*.

Disclosed is also the new use of a NO-releasing NSAID in combination with an acid susceptible proton pump inhibitor for the treatment of bacterial infections.

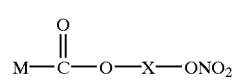

I

17 Claims, No Drawings

USE OF COMPOUNDS AS ANTIBACTERIAL AGENTS

CROSS REFERENCE TO RELATED APPLICATIONS

The present application represents U.S. national stage of international application PCT/SE00/01071, which has an international filing date of May 25, 2000, and which was published in English under PCT Article 21(2) on Dec. 7, 2000. The international application claims priority to SE 9902027-3, filed on Jun. 1, 1999, and SE 9904704-5, filed on Dec. 21, 1999.

FIELD OF THE INVENTION

The present invention is directed to a new use of nitric oxide-releasing Non Steriodal Antiinflammatory Drugs (NO-releasing NSAIDs). More particularly the invention is directed to the use of NO-releasing NSAIDs for the manufacture of a medicament for the treatment of bacterial infections, paticularly caused or mediated by *Helicobacter pylori* as well as a combination with acid susceptible proton pump inhibitors for the treatment of bacterial infections.

BACKGROUND OF THE INVENTION AND PRIOR ART

NSAIDs, are among the most commonly prescribed and used drugs worldwide. Despite the therapeutic benefits of NSAIDs, their use is limited. The use of NSAIDs may lead to gastric mucosal damage due to inhibited production of prostaglandins which increases the risk of gastrointestinal side-effects.

A recent proposal for reducing the side-effects associated with NSAIDs treatment is to use nitric oxide-releasing NSAID derivatives (NO-releasing NSAIDs) (del Soldato P et al., *NO-releasing NSAID:s, A novel class of safer and effective antiinflammatory agents; Inflammopharmacology*, 1996; 4; 181–188). NO-releasing NSAIDs reduce the gastrointestinal side-effects but still have the pharmacological activity characteristic of the frequently used NSAIDs.

NO-releasing NSAIDs and pharmaceutically acceptable salts thereof are for instance described in WO 94/04484, WO 94/12463, WO 95/09831 and WO 95/30641.

*Helicobacter pylori* is a gram-negative spirilliform bacteria which colonises in the gastric mucosa. The relationship between gastrointestinal disorders and infections with *Helicobacter pylori* proposed in 1983 by Warren (Warren J R Lancet 1983; 1.1273) is well established today.

A number of different therapies have been proposed for the treatment of *Helicobacter pylori* infections. Combination therapies are commonly used. The most commonly used comprise a proton pump inhibitor in combination with one or more antibacterial compounds such as claritromycin and amoxicillin. For instance WO 93/00327 discloses the combination of a substance with inhibiting effect on the gastric acid secretion which increases the intragastric pH, and an acid degradable antibacterial compound. Some of these therapies also comprise a bismuth compound, se for instance WO 98/03219 and WO 98/22117, which latter application discloses a composition containing bismuth, an antimicrobial agent and a non-steriodal antiinflammatory agent for the treatment of gastrointestinal disorders caused or mediated by *Helicobacter pylori*.

In view of the vast number of the population suffering from gastrointestinal disorders caused or mediated by bacterial infections, such as *Helicobacter pylori* infections, and also in view of the fact that many bacterial strains develop a resistance to commonly used antibiotics, a continuing need exists for a safe and effective medicament having an antibacterial effect, especially for the treatment of *Helicobacter pylori* infections.

OUTLINE OF THE INVENTION

It has now surprisingly been found that NO-releasing NSAIDs have an antibacterial effect, which makes them useful for the treatment of bacterial infections.

The present invention is related to the use of a NO-releasing NSAID as well as pharmaceutically acceptable salts or enantiomers thereof, for the manufacture of a medicament for the treatment of bacterial infections.

Preferably the NO-releasing NSAID is defined by the formula I $$M-\overset{\overset{\displaystyle O}{\|}}{C}-O-X-ONO_2 \qquad I$$

wherein M is selected from anyone of

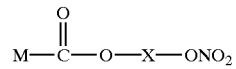

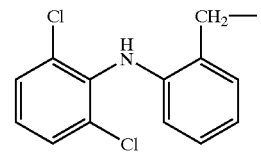

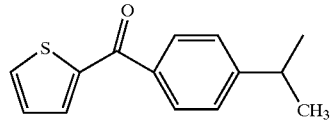

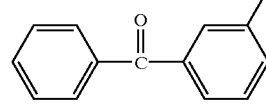

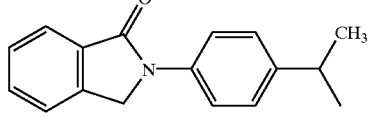

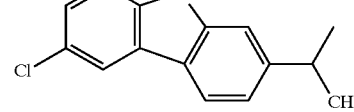

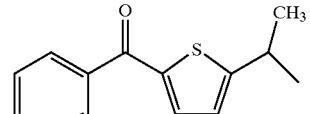

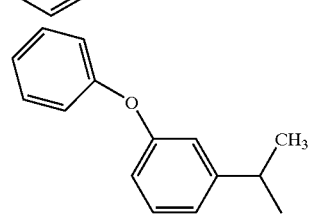

-continued

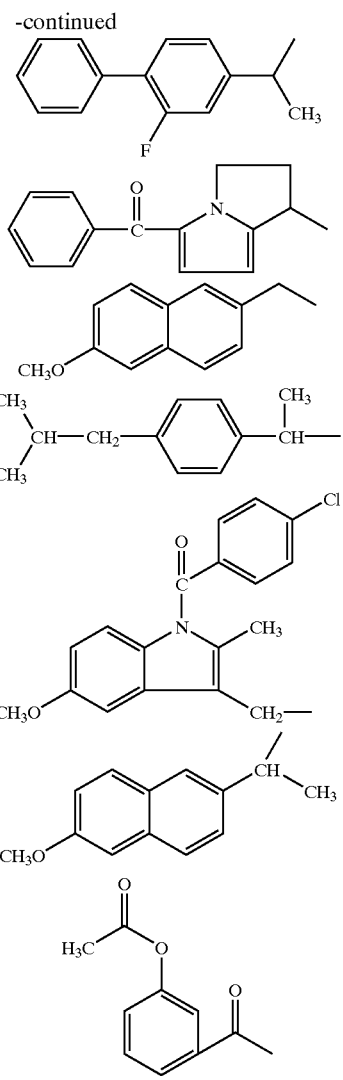

and X is a spacer, i.e. a compound forming a bridge between the nitrogen oxide donating group and the NSAID moiety, or a pharmaceutically acceptable salt or enantiomer thereof;

X is preferably selected from linear, branched or cyclic —$(CH_2)$—$_n$ wherein n is an integer of from 2 to 10; —$(CH_2)_m$—O—$(CH_2)_p$— wherein m and p are integers of from 2 to 10; and —$CH_2$—$pC_6H_4$—$CH_2$—.

M is not limited by the above definition but may be any other compound giving the corresponding NSAID by hydrolysis of the compound according to formula I.

In a preferred embodiment of the invention M is selected from

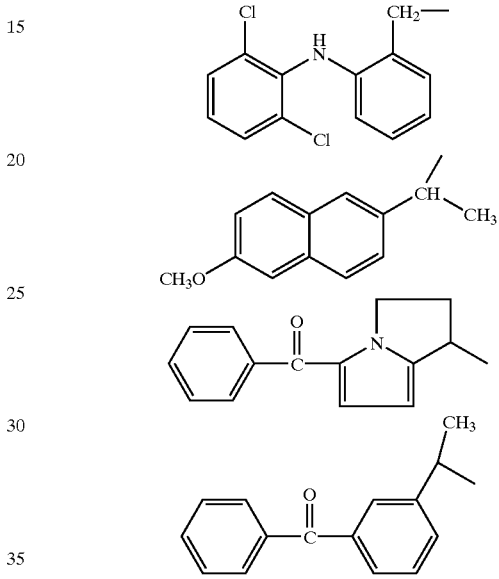

and X is selected from linear —$(CH_2)_n$— wherein n is an integer of from 2 to 6; —$(CH_2)_2$—O—$(CH_2)_2$— and —$CH_2$—$pC_6H_4$—$CH_2$—.

In an even more preferred embodiment of the invention the NO-releasing NSAID is a compound according to any one of the formulas

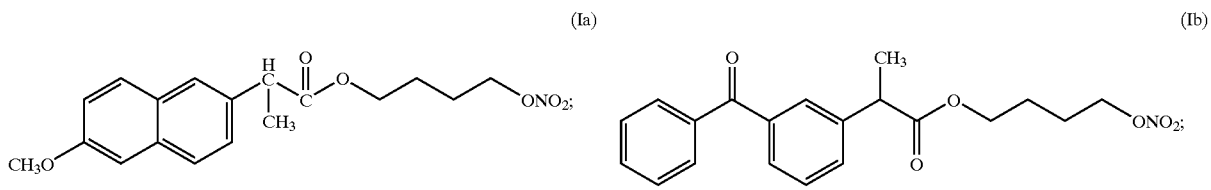

(Ia) (Ib)

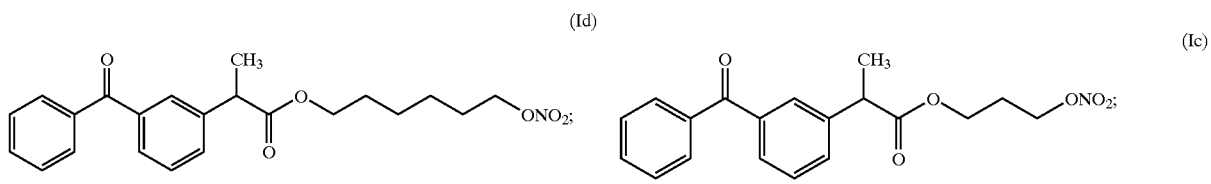

(Id) (Ic)

-continued
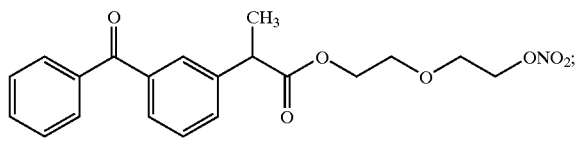 (Ie)
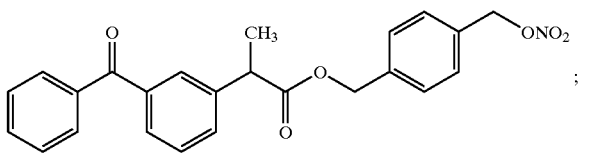 (If)
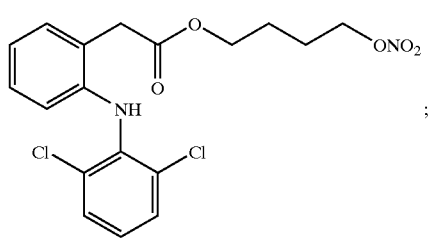 (Ig)
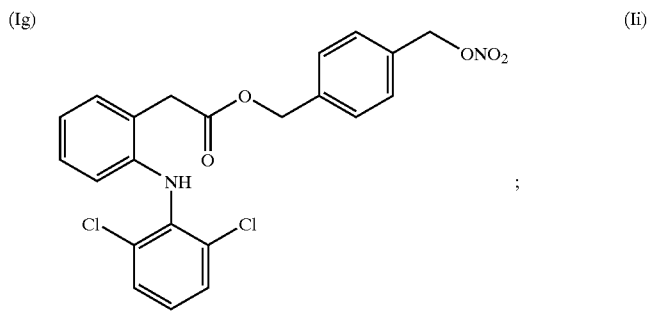 (Ii)
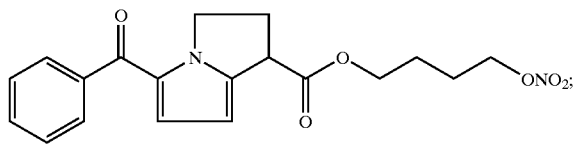 (Ij)
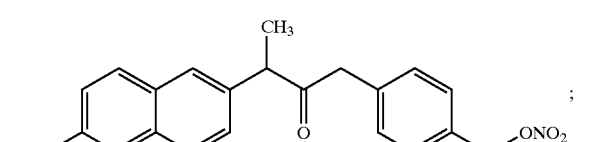 (Ik)
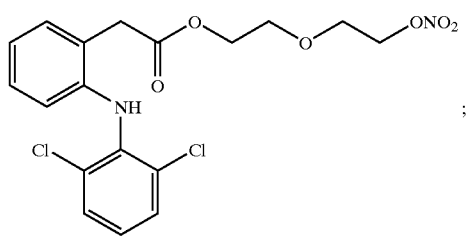 (Il)
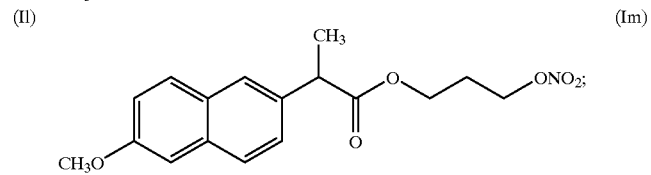 (Im)
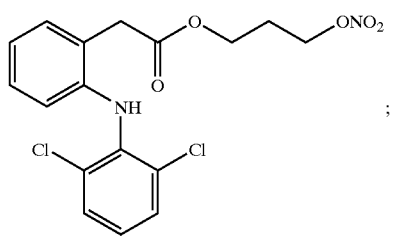 (In)
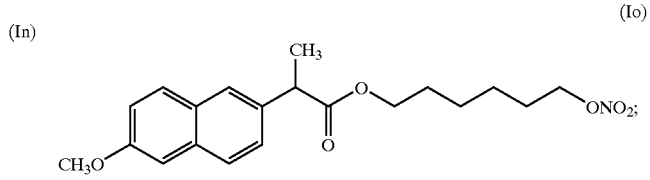 (Io)
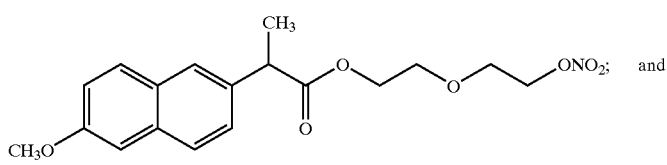 (Ip) and
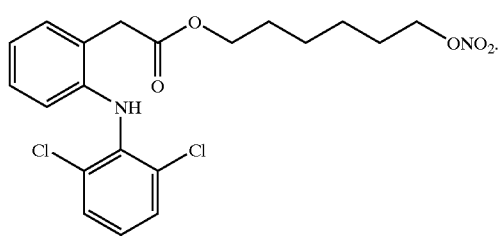 (Iq)

In a particularly preferred embodiment of the invention the NO-releasing NSAID is a compound according to formula Ia.

A further aspect of the invention is the use of a NO-releasing NSAID, preferably a compound of the formula I above, in the manufacture of a medicament for use in the treatment of *Helicobacter pylori* infections, especially in the treatment of gastrointestinal disorders caused or mediated by *Helicobacter pylori*.

Still a further aspect of the invention is a method for the treatment of bacterial infections, in particular *Helicobacter pylori* infections, whereby an effective amount of a medicament comprising a NO-releasing NSAID, preferably a compound of the formula I, as active agent is administered to a subject suffering from said bacterial infection.

Also a pharmaceutical formulation suitable for use in the treatment of bacterial infections, which formulation comprising a NO-releasing NSAID, preferably a compound of the formula I, is within the scope of the invention.

Furthermore, the invention is related to the use of a NO-releasing NSAID, preferably a compound of the formula I, in combination with an acid susceptible proton pump inhibitor or a salt thereof or an enantiomer or a salt of the enantiomer in the manufacture of pharmaceutical formulations intended for simultanous, separate or sequential administration in the treatment of bacterial infections, especially *Helicobacter pylori* infections.

The invention may be applied in combination with other agents generally associated with treatment of bacterial infections, such as for instance antibacterial agents.

An acid susceptible proton pump inhibitor is, for instance, a compound of the general formula II

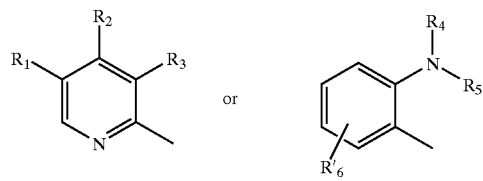

wherein

Het$_1$ is

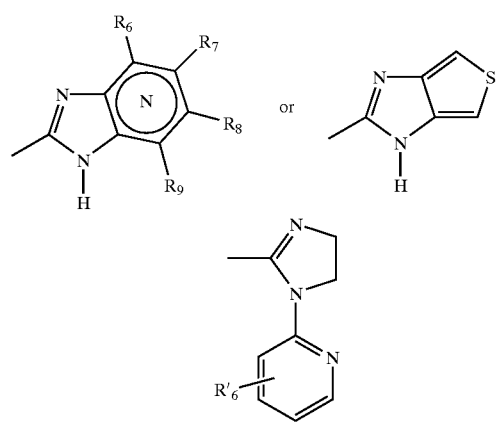

Het$_2$ is

X =

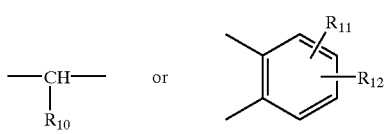

wherein

N in the benzimidazole moiety means that one of the carbon atoms substituted by R$_6$–R$_9$ optionally may be exchanged for a nitrogen atom without any substituents;

R$_1$, R$_2$ and R$_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;

R$_4$ and R$_5$ are the same or different and selected from hydrogen, alkyl and aralkyl;

R$_6$' is hydrogen, halogen, trifluoromethyl, alkyl and alkoxy;

R$_6$–R$_9$ are the same or different and selected from hydrogen, alkyl, alkoxy, halogen, halo-alkoxy, alkylcarbonyl, alkoxycarbonyl, oxazolyl, trifluoroalkyl, or adjacent groups R$_6$–R$_9$ form ring structures which may be further substituted;

R$_{10}$ is hydrogen or forms an alkylene chain together with R$_3$ and

R$_{11}$ and R$_{12}$ are the same or different and selected from hydrogen, halogen or alkyl, alkyl groups, alkoxy groups and moities thereof. The substituents may be branched or straight C$_1$–C$_9$ —chains or comprise cyclic alkyl groups, such as cycloalkyl-alkyl.

Examples of proton pump inhibitors according to formula II are

Omerprazole

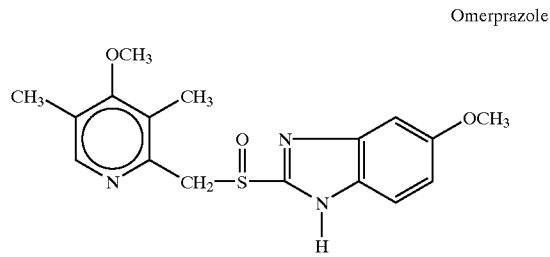

Lansoprazole

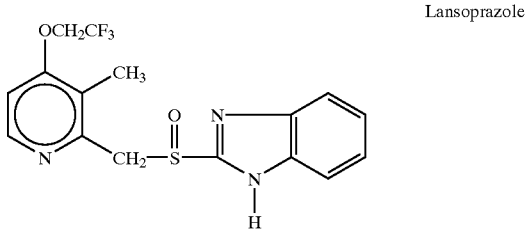

-continued

Pantoprazole

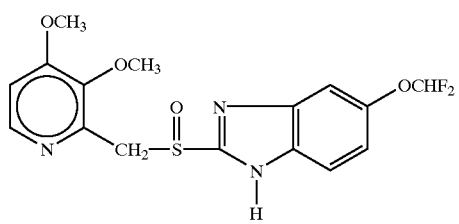

Pariprazole

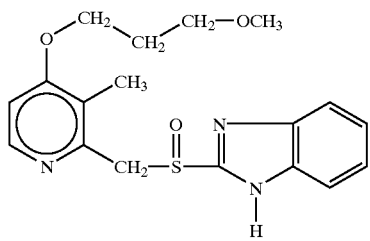

Leminoprazole

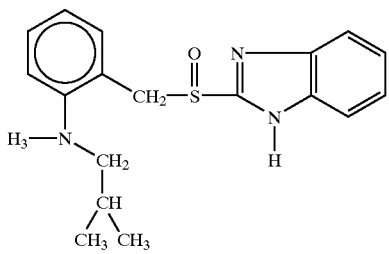

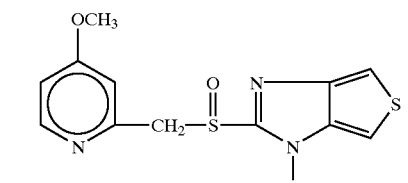

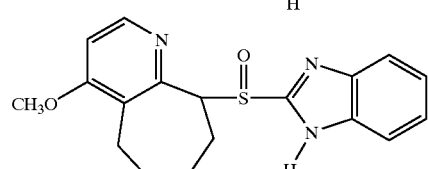

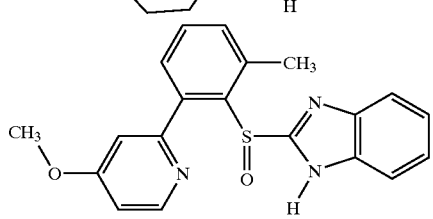

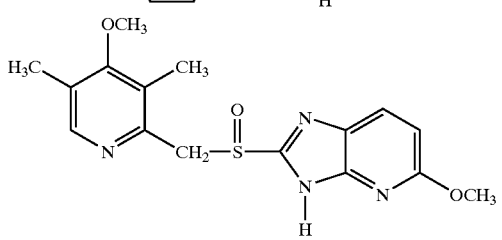

-continued

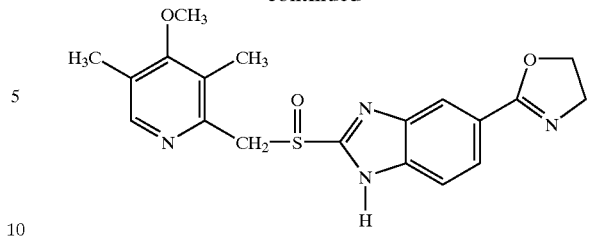

The proton pump inhibitor may also be used in the form of a pharmaceutical acceptable salt or a single enantiomer in the claimed combination.

Preferably the proton pump inhibitor omeprazole, or an alkaline salt of omeprazole, such as the magnesium salt, or (S)-omeprazole or an alkaline salt of (S)-omeprazole, such as the magnesium salt is used in the claimed combination.

Suitable proton pump inhibitors are for example disclosed in EP-A1-0005129, EP-A1-174 726, EP-A1-166 287, GB 2 163 747 and WO90/06925, and further the especially suitable compounds are described in WO95/01977 and WO94/27988.

According to the invention there is further provided a method for treating bacterial infections, particularly *Helicobacter Pylori* infections, which method comprises simultaneous, separate or sequential administration to a subject suffering from a bacterial infection one or more pharmaceutical formulations comprising a NO-releasing NSAID, preferably a compound according to the formula I, and an acid susceptible proton pump inhibitor. Also pharmaceutical formulations for simultaneous, separate or sequential administration to be used in the treatment of bacterial infections, which formulations comprise an NO-releasing NSAID, preferably a compound of the formula I and an acid susceptible proton pump inhibitor are within the scope of the invention.

The NO-releasing NSAID alone or in combination with an acid susceptible compound may be in a dosage form administered orally, rectally, epidurally, intravenously, intramuscularly, subcutaneously, by infusion, nasally or any other way suitable for administration. Preferably the active compound(-s) is administered orally.

The active compound(-s) are administered one to several times a day, preferably once or twice daily. The typical daily dose of the active compound(-s) varies and will depend on various factors such as the individual requirements of the patients, the mode of administration and disease. In general each dosage form will comprise 0.5–5000 mg, preferably 5–1000 mg, of the NO-releasing NSAID. If a combination with a proton pump inhibitor is used 0.5–5000 mg of the NO-releasing NSAID, and 0.1–200 mg of the proton pump inhibitor will be comprised in each dosage form, or in two separate dosage forms. Preferably, the amount of the NO-releasing NSAID in each dosage form is 5–1000 mg, and the amount of the proton pump inhibitor 10–80 mg.

DETAILED DESCRIPTION OF THE INVENTION

The invention is described in more detail by the following non-limiting examples.

The examples below support that NO-releasing NSAIDs are active against *Helicobacter pylori*, and that the antibacterial activity is concentration dependent.

EXAMPLE 1

Strain: *Helicobacter pylori* Reference Strain NCTC 11 637 (National Type Culture Collection, from Smittskyddsinstitutet in Solna, Sweden), an Antibiotic Sensitive Reference Strain Substance:

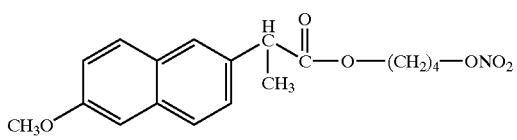

Ia

*Helicobacter pylori* was grown on blood agar plates, having a diameter of 90 mm. for three days under microaerophilic conditions at 37° C. The bacteria were suspended in PBS (phosphate buffer saline) to approximately $10^8$ cfu/ml. Approximately 2 ml of the suspension was added to one agar plate and spread even on the surface of the agar. Overflow was removed with a syringe. Wells, like small holes, 3 mm in diameter, were made in the agarplate by removing agar. Three wells per plate were made. A stock solution of a compound of the formula Ia having the concentration 100000 μg/ml was prepared. 30 μl of the solution was added to the wells. The plates were incubated for four days before they were checked for inhibition zones around the wells.

Result: The inhibition zone around each well was large, i.e. it was not possible to measure the diameter of the zone.

EXAMPLE 2

Strain: *Helicobacter Pylori* Reference Strain NCTC 11 637 (see Example 1), an Antibiotic Sensitive Reference Strain Substance:

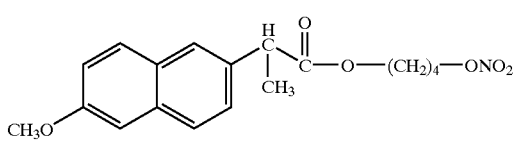

Ia

The plates with the wells were prepared according to Example 1.

A stock solution of a compound of the formula Ia having the concentration 10000 μg/ml was prepared. 30 μl of the solution was added to the wells. The plates were incubated for four days before they were checked for inhibition zones around the wells. Result: The inhibition zone around each well was large, i.e. it was not possible to measure the diameter of the zone.

EXAMPLE 3

Strain: *Helicobacter pylori* reference strain NCTC 11 637, an Antibiotic Sensitive Reference Strain (see Example 1)

Substance:

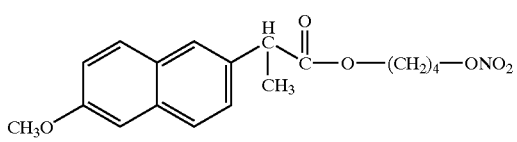

Ia

The plates with the wells were prepared according to Example 1. A stock solution of a compound of the formula Ia having the concentration 1000 μg/ml was prepared. 30 μl of the solution was added to the wells. The plates were incubated for four days before they were checked for inhibition zones around the wells.

Result: The inhibition zone around each well was 13 mm.

EXAMPLE 4

Strain: *Helicobacter pylori* Reference Strain NCTC 11 637, an Antibiotic Sensitive Reference Strain (see Example 1)

Substance:

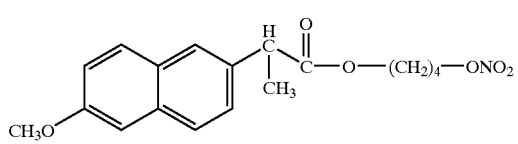

Ia

The plates with the wells were prepared according to Example 1.

A stock solution of a compound of the formula Ia having the concentration 100 μg/ml was prepared. 30 μl of the solution was added to the wells. The plates were incubated for four days before they were checked for inhibition zones around the wells.

Result: The inhibition zone around each well was 10.4 mm.

COMPARATIVE TESTS

EXAMPLE A

Strain: *Helicobacter Pylori* Reference Strain NCTC 11. 637, an Antibiotic Sensitive Reference Strain (see Example 1)

Substance: Naproxen

The plates with the wells were prepared according to Example 1.

A stock solution of Naproxen having the concentration 10000 μg/ml was prepared. 30 μl of the solution was added to the wells. The plates were incubated for four days before they were checked for inhibition zones around the wells.

Result: The inhibition zone around the each well was 16.6 mm.

EXAMPLE B

Strain: *Helicobacter pylori* reference strain NCTC 11 637, an Antibiotic Sensitive Reference Strain (see Example 1)

Substance: Naproxen

The plates with the wells were prepared according to Example 1.

A stock solution of Naproxen having the concentration 1000 μg/ml was prepared. 30 μl of the solution was added to the wells. The plates were incubated for four days before they were checked for inhibition zones around the wells.

Result: No inhibition zones around the wells were formed.

EXAMPLE C

Strain: *Helicobacter Pylori* Reference Strain NCTC 11 637, an Antibiotic Sensitive Reference Strain (see Example 1)

Substance: Naproxen

The plates with the wells were prepared according to Example 1.

A stock solution of Naproxen having the concentration 100 μg/ml was prepared. 30 μl of the solution was added to the wells. The plates were incubated for four days before they were checked for inhibition zones around the wells.

Result: No inhibition zones around the wells were formed.

EXAMPLE D

Strain: *Helicobacter Pylori* Reference Strain NCTC 11 637, an Antibiotic Sensitive Reference Strain (see Example 1)

Substance: S-nitroso-N-acetyl-penicillamin (SNAP)

The plates with the wells were prepared according to Example 1.

A stock solution of SNAP with the concentration 10000 μg/ml was prepared. 30 μl of the solution was added to the wells. The plates were incubated for four days before they were checked for inhibition zones around the wells.

Result: No inhibition zones around the wells were formed.

EXAMPLE E

Strain: *Helicobacter Pylori* Reference Strain NCTC 11 637, an Antibiotic Sensitive Reference Strain (see Example 1)

Substance: Di-methyl-sulphate-oxide (DMSO)

The plates with the wells were prepared according to Example 1.

A solution of DMSO alone with the concentration 20 μg/ml was prepared. 30 μl of the solution was added to the wells. The plates were incubated for four days before they were checked for inhibition zones around the wells.

Result: No inhibition zones around the wells were formed.

What is claimed is:

1. A method for the treatment of a bacterial infection caused or mediated by *Helicobacter pylori*, comprising administering to a patient suffering from said bacterial infection, an effective amount of an NO-releasing NSAID or a pharmaceutically acceptable salt or an enantiomer thereof.

2. A method according to claim 1 wherein the amount of NO-releasing NSAID in each dosage form is 0.5–5000 mg.

3. A method according to claim 2 wherein the amount of NO-releasing NSAID is 5–1000 mg.

4. A method for the treatment of disorders caused or mediated by *Helicobacter pylori*, comprising simultaneously, separately or sequentially administering to a patient suffering from said disorder, an effective amount of an NO-releasing NSAID and an acid susceptible proton pump inhibitor or a salt thereof or an enantiomer or a salt of the enantiomer.

5. A method according to claim 4 wherein the amount of NO-releasing NSAID is 0.5–5000 mg and the amount of proton pump inhibitor is 0.1–200 mg together in one dosage form or in two separate dosage forms.

6. A method according to claim 5 wherein the amount of NO-releasing NSAID is 5–1000 mg and the amount of proton pump inhibitor is 10–80 mg.

7. A method according to claim 4 wherein the acid susceptible proton pump inhibitor is a compound of the formula II

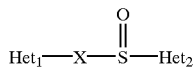

II wherein $Het_1$ is

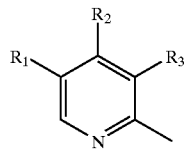 or 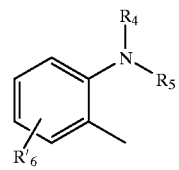

$Het_2$ is

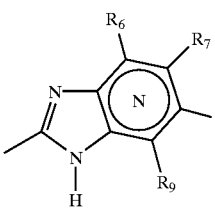 or 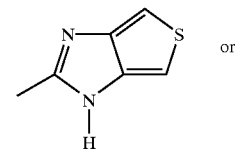 or

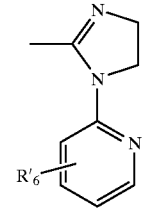

X =

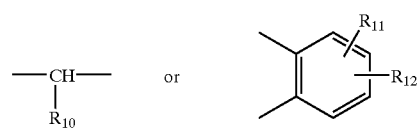

wherein

N in the benzimidazole moiety means that one of the carbon atoms substituted by $R_6$–$R_9$ optionally may be exchanged for a nitrogen atom without any substituents;

$R_1$, $R_2$ and $R_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;

$R_4$ and $R_5$ are the same or different and selected from hydrogen, alkyl and aralkyl;

R6' is hydrogen, halogen, trifluoromethyl, alkyl and alkoxy;

$R_6$–$R_9$ are the same or different and selected from hydrogen, alkyl, alkoxy, halogen, halo-alkoxy, alkylcarbonyl, alkoxycarbonyl, oxazolyl, trifluoroalkyl, or adjacent groups $R_6$–$R_9$ form ring structures which may be further substituted;

$R_{10}$ is hydrogen or forms an alkylene chain together with $R_3$ and $R_{11}$ and $R_{12}$ are the same or different and selected from hydrogen, halogen or alkyl, alkyl groups, alkoxy groups and moities thereof, they may be branched or straight $C_1$–$C_9$— chains or comprise cyclic alkyl groups, such as cycloalkyl-alkyl.

8. A method according to claim 7 wherein the acid susceptible proton pump inhibitor is pantoprazole or a pharmaceutically acceptable salt thereof or an enantiomer or a salt of the enantiomer.

9. A method according to claim 7 wherein the acid susceptible proton pump inhibitor is selected from omeprazole. an alkaline salt thereof, (S)-omeprazole and an alkaline salt thereof.

10. A method according to claim 7 wherein the acid susceptible proton pump inhibitor is lansoprazole or a pharmaceutically acceptable salt thereof or an enantiomer or a salt of the enantiomer.

11. A pharmaceutical formulation according to claim 9 or 10 wherein the NO-releasing NSAID is a compound of the formula I

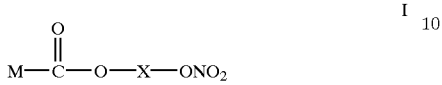

wherein M is selected from

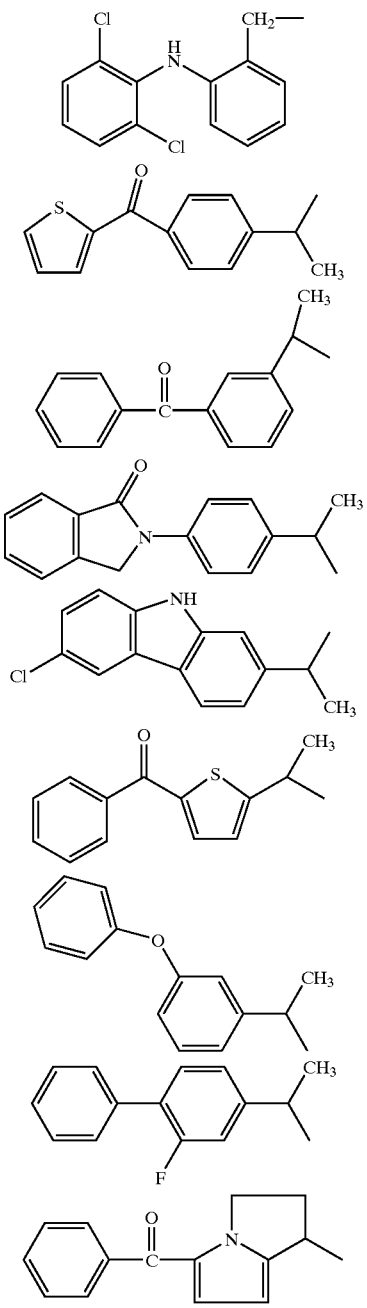

-continued

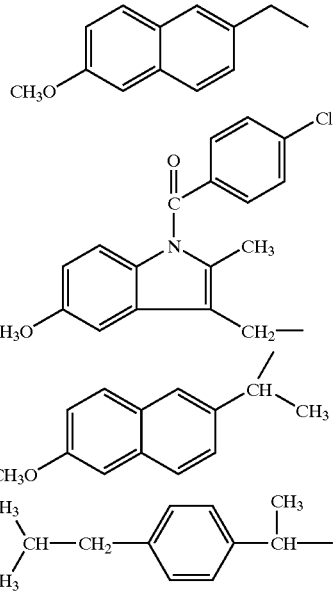

and X is selected from linear, branched or cyclic —(CH$_2$)$_n$— wherein n is an integer of from 2 to 10; —(CH$_2$)$_m$—O—(CH$_2$)$_p$— wherein m and p are integers of from 2 to 10; and —CH$_2$—pC$_6$H$_4$—CH$_2$—;

or a pharmaceutically acceptable salt or enantiomer thereof.

12. A method according to claim 1 or 4 wherein the NO-releasing NSAID is a compound of the formula I

wherein M is selected from

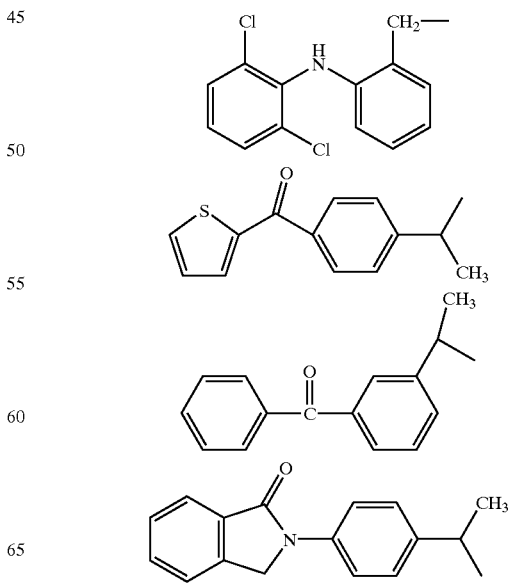

-continued

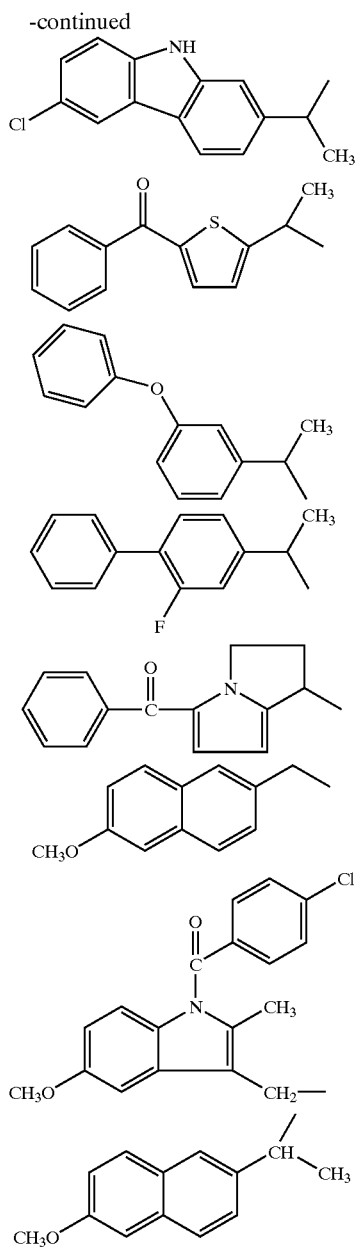

-continued

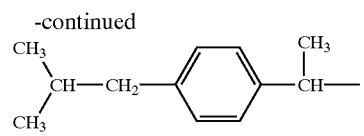

and X is selected from linear, branched or cyclic —(CH$_2$)$_n$— wherein n is an integer of from 2 to 10;

—(CH$_2$)$_m$—O—(CH$_2$)$_p$— wherein m and p are integers of from 2 to 10; and —CH$_2$—pC$_6$H$_4$—CH$_2$—, or a pharmaceutically acceptable salt or enantiomer thereof.

13. A method according to claim 12 wherein M in formula I is selected from

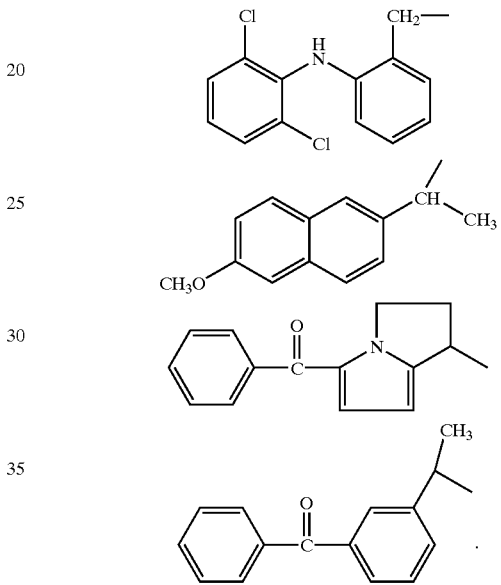

14. A method according to claim 12 wherein X in formula I is selected from linear —(CH$_2$)$_n$— wherein n is an integer of from 2 to 6, —(CH$_2$)$_2$—O—(CH$_2$)$_2$— and —CH$_2$—p C$_6$H$_4$—CH$_2$—.

15. A method according to claim 12 wherein NO-releasing NSAID is a compound according to any one of the formulas Ia–Iq

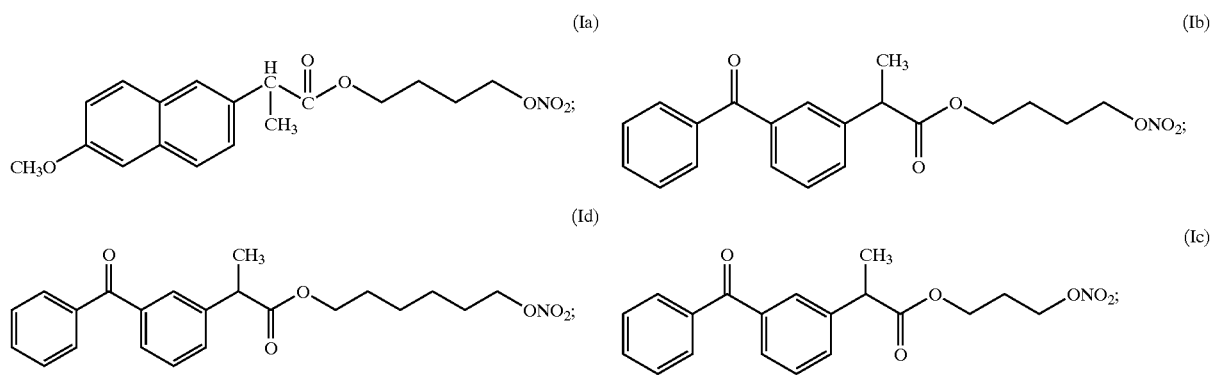

-continued
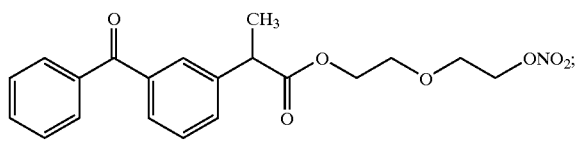 (Ie)
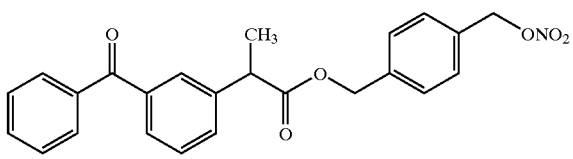 (If)
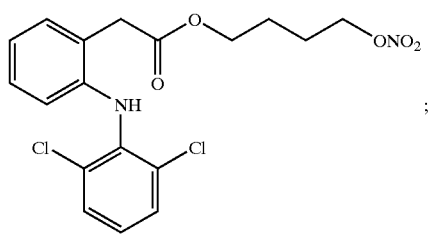 (Ig)
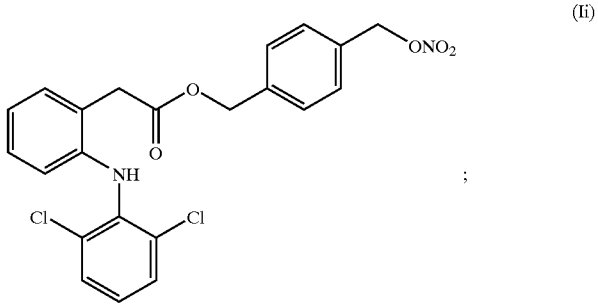 (Ii)
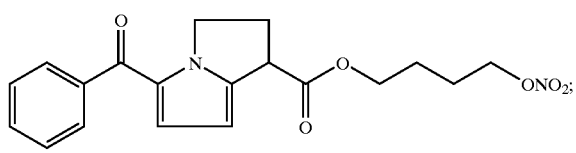 (Ij)
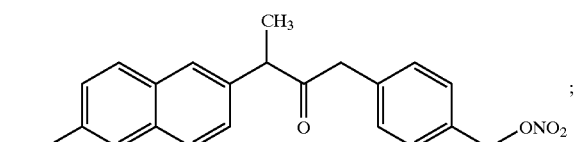 (Ik)
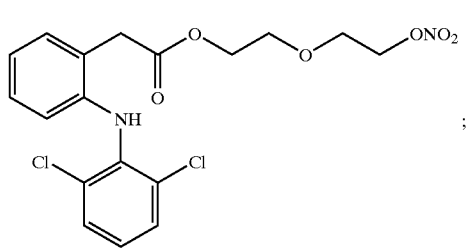 (Il)
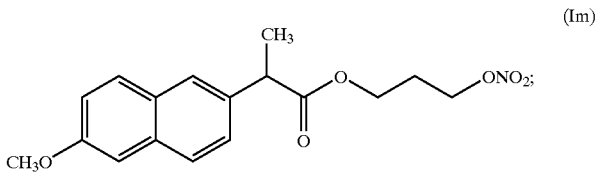 (Im)
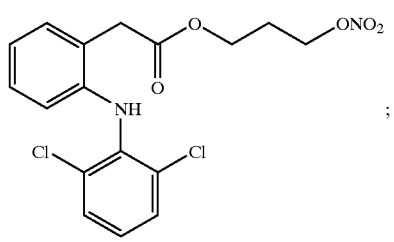 (In)
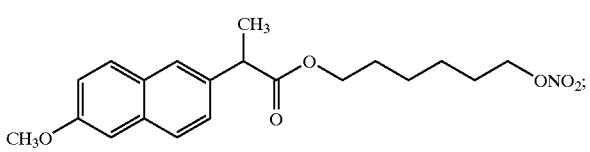 (Io)
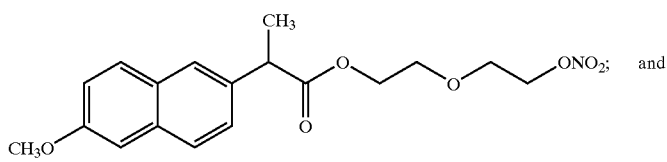 (Ip) and
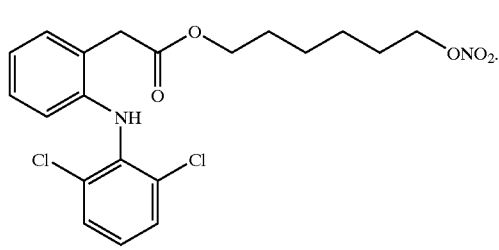 (Iq)

16. A method according to claim 15 wherein the NO-releasing NSAID is a compound of formula Ia

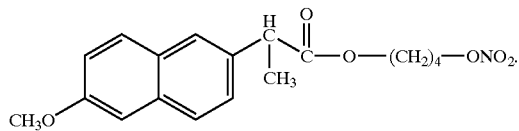

(Ia)

17. A pharmaceutical formulation suitable for use in the treatment of disorders caused or mediated by *Helicobacter pylori*, comprising an NO-releasing NSAID and an acid susceptible proton pump inhibitor or a salt thereof or an enantiomer or a salt of the enantiomer as active agents.

* * * * *